United States Patent [19]

Schnall

[11] 4,251,214
[45] Feb. 17, 1981

[54] CLAMPING HANDLE FOR TOOTH ROOT CANAL INSTRUMENTS

[75] Inventor: Manfred Schnall, Unterhaching, Fed. Rep. of Germany

[73] Assignee: Vereinigte Dentalwerke, Munich, Fed. Rep. of Germany

[21] Appl. No.: 873,624

[22] Filed: Jan. 30, 1978
(Under 37 CFR 1.47)

[30] Foreign Application Priority Data

Jan. 28, 1977 [DE] Fed. Rep. of Germany ....... 2703637

[51] Int. Cl.³ ................................................. A61C 0/00
[52] U.S. Cl. .................................... 433/147; 433/102; 30/329
[58] Field of Search .................. 433/147, 102; 15/143; 29/80; 279/28, 1 W; 30/366, 367, 368, 329

[56] References Cited

U.S. PATENT DOCUMENTS

| | | | |
|---|---|---|---|
| 1,404,519 | 2/1922 | Gilbert | 433/102 |
| 2,169,107 | 8/1939 | Martin | 279/28 |
| 2,170,942 | 8/1939 | Euasic | 279/28 |
| 2,604,693 | 7/1952 | Schiersfead | 433/147 |

Primary Examiner—Robert Peshock
Attorney, Agent, or Firm—William A. Drucker

[57] ABSTRACT

A clamping handle for holding a tooth root canal instrument is of the kind with a screw head formed thereon and an axial bore through the handle body and the screw head for the accommodation of an instrument shaft, a screw element screwable onto the screw head and also provided with a bore aligned with the axial bore, and a clamping element which can be pressed against the instrument shaft by screwing the screw element onto the screw head. The improvement is that a clamping disk is inserted between a pressing surface of the screw head and an approximately parallel pressing surface of the screw element, the clamping disk having a through-bore, to receive an instrument shaft, which is inclined with respect to the plane of the disk but is aligned with the axial bore of the handle body.

6 Claims, 3 Drawing Figures

CLAMPING HANDLE FOR TOOTH ROOT CANAL INSTRUMENTS

SPECIFICATION

This invention relates to a clamping handle, for holding tooth root canal instruments, of the kind having a handle body, a screw head thereon, an axial bore passing through the handle body and the screw head for the accommodation of an instrument shaft, and a screw element screwable onto the screw head, said screw element also being provided with a bore aligned with the axial bore, and with a clamping element which, when the screw element and the screw head are screwed together, can be pressed against the instrument shaft.

BACKGROUND OF THE INVENTION

With a known clamping handle of this kind, the clamping element is formed by segment-like clamping jaws of the screw head. In order to be able to exert a radial pressure on these clamping jaws, the screw head and a screw nut must be developed conically (DT-PS 929 867). For reasons of strength, the clamping jaws should not be too weak. Their deformation, for clamping the instrument therefore requires a strong tightening of the screw nut. This in return results later in the screw nut often not being able to be loosened with bare fingers. On the other hand, a screw joint which is too slack does not guarantee a tight fit of the instrument. Furthermore, the development of clamping jaws and a threaded cone on a relatively small working part makes the known clamping handle complicated and expensive.

OBJECT OF THE INVENTION

It is therefore the object of the invention to provide a clamping handle which is simpler and cheaper in its manufacture, and whose clamping element is more effective.

SUMMARY OF THE INVENTION

According to the present invention, this object is achieved by a clamping handle of the kind mentioned above being provided with a clamping disk inserted between a front end pressure surface of the screw head and an almost parallel pressure surface of the screw element, this clamping disk being provided with a through-bore for the instrument shaft, this bore being inclined towards the disk plane but aligned to the axial bore of the handle body.

When the screw element is screwed onto the screw head, the clamping disk is raised by the adjoining pressure surfaces from its original inclined position which it occupies because of the inclined through-bore, with its bore thus being canted against the instrument shaft. This results in clamping of the instrument shaft. Although even this clamping handle cannot do without any threaded parts, these are considerably simpler than the development of a screw cone with clamping jaws. A further advantage of the clamping element according to the invention is that the clamping disk causes an edge contact which results in a considerably more effective clamping. Accordingly, there is no risk that the instrument might shift, even if the screw cap is only slightly tightened. Finally, it is evident that the clamping disk canted under pressure between the screw element and the screw head acts like a counter disk and thus prevents an automatic slackening of the screw joint when handling the instrument held by the clamping handle.

If the screw head is provided with an external thread, the screw element may be in the form of a screw cap with an internal thread. However, even a screw bolt which can be screwed into the screw head provided with an internal thread, can be a suitable screw element.

The screw head and screw element are advantageously formed on the instrument side of the handle body, the handle part thus being extended and the possibility of ad adjustment of the instrument in the clamping handle being increased.

BRIEF DESCRIPTION OF THE DRAWINGS

Further features of the invention will be apparent from the following description of an embodiment shown in the accompanying drawing.

In the drawing.

DESCRIPTION OF THE PREFERRED EMBODIMENT

Figure 1:
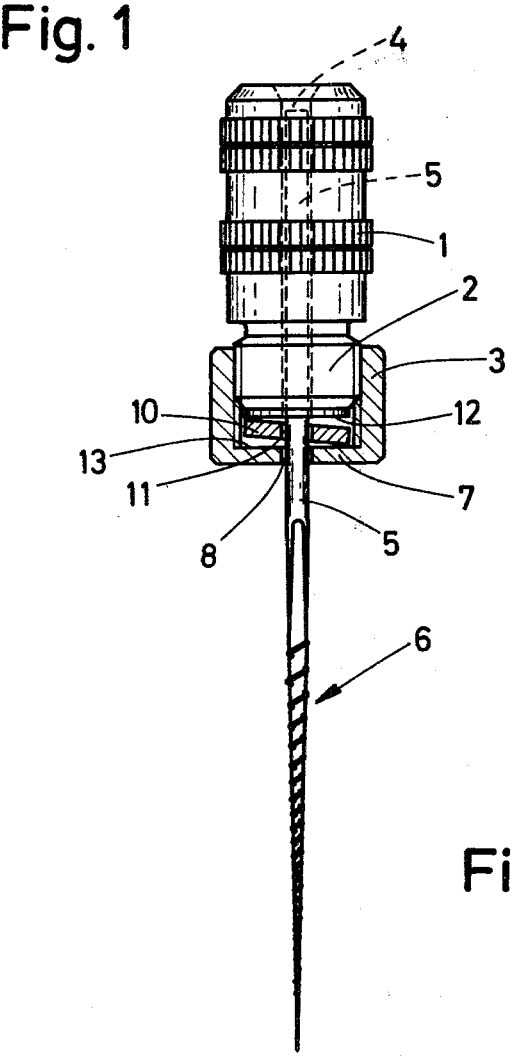
FIG. 1 is a view of a clamping handle with inserted instrument in an adjustable position.
Figure 2:
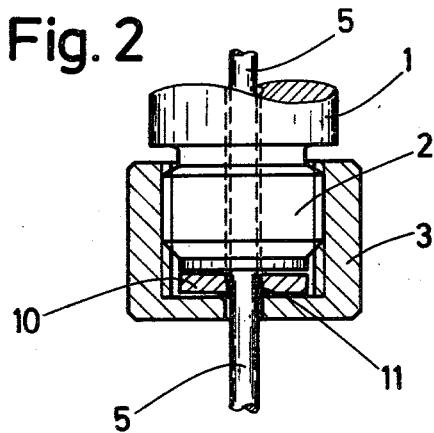
FIG. 2 is a section of FIG. 1 with clamped-in instrument.

According to FIGS. 1 and 2, the clamping handle consists of a handle body 1 with a screw head 2 and a screw cap 3 which, with its internal thread, can be screwed onto the screw head 2 with its external thread. The handle body 1 and the screw head 2 have an axial bore 4 in which an instrument shaft 5 of a tooth root canal instrument 6 is held adjustably with slight play. The screw cap 3 is also provided with a bore 8 in its wall 7 which may also be larger than the axial bore 4. In order to lock the instrument in the clamping handle, a clamping disk 10 is inserted between the screw head 2 and the screw cap 3. This clamping disk is provided with a through-bore 11 for the instrument shaft to pass through. Since this through-bore 11 does not extend vertically to the plane of the disk but is inclined to it, the bore 11 occupies, in its original position as shown in FIG. 1, an inclined position with respect to the instrument shaft. The front end of the screw head 2 and the inner surface of the screw cap wall 7 have respective pressure surfaces 12, 13. When the screw cap 3 is screwed onto the screw head 2, the clamping disk 10 is pushed out of its inclined position by the pressure surfaces 12, 13 and is subjected to a more or less heavy deformation (FIG. 2). This results in a canting of the through-bore 11 against the instrument shaft and a clamping of the instrument in the clamping handle. To release the clamped-in instrument, it is merely necessary to slacken back the screw cap, this resulting in the clamping disk being able to return to its original position. The instrument can again be adjusted or pulled out completely from the axial bore. Since the clamping disk is centered within the screw cap, it is possible to insert the instrument shaft through the clamping disk lying loosely between screw head and screw cap and to insert it into the clamping handle even without having to take off the screw cap.

Figure 3:
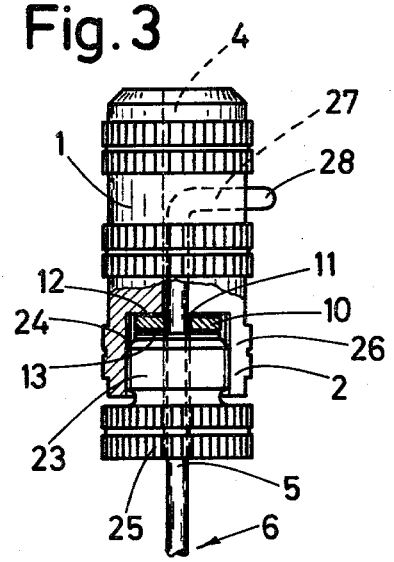
FIG. 3 is a view of a clamping handle with a different type of screw joint.

The clamping handle according to FIG. 3 differs from the one described above in its screw element which now has the form of a screw bolt 23 with an external thread which can be screwed into a bore 24 of a screw head 2 provided with an internal thread. A knurled ring 25 of the screw bolt 23 makes this adjustment easier.

The handle body 1 of FIG. 3 is furthermore provided with an elongated through-slot 26 which extends right up to the axial bore 4 and also has the same width as the latter. In this elongated slot there can run an angular end extension 27 whose end 28 facilitates the setting of the instrument depth, in particular if the handle body is provided with a measuring scale.

The clamping disk will advantageously consist of a resiliently deformable steel, e.g. spring steel. The throughbore 11 will generally not be much larger than the diameter of the instrument shaft. It can be larger if it is steeply inclined in relation to the normal to the plane of the disk so that its clamping edges make a larger angular movement whilst the clamping disk is being raised, until they finally engage with the instrument shaft.

The invention is not restricted to the described embodiment. The clamping disk with screw head and screw element may, for example, also be formed on that side of the handle body 1 looking away from the instrument. The clamping element could also be accommodated between the sections of a two-part screwable handle body. The screw element may also be provided with a lock which prevents it from being removed from the screw head. For this purpose, the screw cap could for example be provided on its inner side with an overlapping edge. A similar safeguard is also possible on the handle disk 25 of FIG. 3 (not illustrated).

The handle body 1 will generally be of cylindrical shape and will have knurls on its outer surface. The screw cap and the handle disk may also be formed in this way. Advantageously, however, they have the form of a polygonal nut.

The clamping handle parts may be of metal as well as of plastic. In particular a plastic clamping handle can readily be manufactured in colour according to a colour code corresponding to the instrument sizes.

The fact that the handle body has always been shown in the embodiments as a manual handle does not mean that the invention is restricted to this. The clamp joint according to the invention is, on the contrary, also possible on an insert or angle piece for manually or motor operated devices.

I claim:

1. A clamping handle, for holding a tooth root canal instrument, comprising:
   (i) a handle body with a screw head formed thereon and including an axial bore through the handle body and the screw head for the accommodation of an instrument shaft,
   (ii) a screw element threadable onto the screw head and including a bore aligned with the axial bore of the handle body, said bore of the screw element being of cross-section adapted to receive the instrument shaft with clearance, and
   (iii) a clamping disc having a median plane and opposed major faces, said disc being disposed between the screw head and the screw element with one of its major faces abutting a radial surface of the screw head and the other of its major faces abutting an approximately parallel radial face of the screw element, said clamping disc including a through-bore adapted to receive the instrument shaft with clearance, the axis of said bore of the clamping disc being inclined with respect to a normal to the median plane of the disc, the cross-section of said through-bore relative to the cross-section of the shaft being such that, upon movement of the disc in the direction towards placing its median plane parallel with said radial surfaces, the portion of the disc bounding said through-bore will abut against the shaft.

2. A clamping handle, according to claim 1, wherein the diameter of the clamping disk is only slightly smaller than the inner diameter of the screw element.

3. A clamping handle, according to claim 1, wherein the clamping disk is of spring steel.

4. A clamping handle, according to claim 1, wherein the screw head is formed on the instrument side of the handle body.

5. A clamping handle, according to claim 1, wherein the screw element is a screw cap.

6. A clamping handle, according to claim 1, wherein the screw element is a screw bolt with a handle disk.

* * * * *